United States Patent [19]

Nuovo et al.

[11] Patent Number: 5,538,871
[45] Date of Patent: Jul. 23, 1996

[54] IN SITU POLYMERASE CHAIN REACTION

[75] Inventors: Gerard J. Nuovo, Calverton, N.Y.; Will Bloch, El Cerrito, Calif.

[73] Assignees: Hoffmann-La Roche Inc., Nutley, N.J.; Research Foundation of State of New York, Albany, N.Y.

[21] Appl. No.: 390,256

[22] Filed: Feb. 17, 1995

Related U.S. Application Data

[63] Continuation of Ser. No. 733,419, Jul. 23, 1991, abandoned.

[51] Int. Cl.$^6$ .............................. C12P 19/34; C12Q 1/68; C07H 21/04; C12N 15/00
[52] U.S. Cl. .............................. 435/91.2; 435/6; 435/91.1; 536/24.32; 536/24.33; 536/25.3; 935/77; 935/78
[58] Field of Search .................................. 435/5, 6, 91.1, 435/91.2; 935/16, 77, 78; 536/24.32, 24.33, 25.3

[56] References Cited

U.S. PATENT DOCUMENTS

| | | | |
|---|---|---|---|
| 4,683,195 | 7/1987 | Mullis et al. | 435/6 |
| 4,965,188 | 10/1990 | Mullis et al. | 435/6 |
| 5,021,335 | 6/1991 | Tecott et al. | 435/6 |
| 5,188,963 | 2/1993 | Stapleton | 435/209 |
| 5,230,997 | 7/1993 | Frenkel | 435/5 |
| 5,273,881 | 12/1993 | Sena et al. | 425/6 |
| 5,281,516 | 1/1994 | Stapleton et al. | 435/3 |

FOREIGN PATENT DOCUMENTS

| | | | |
|---|---|---|---|
| 0236069 | 9/1987 | European Pat. Off. | |
| 9106679 | 5/1991 | WIPO | C12Q 1/68 |

OTHER PUBLICATIONS

Nagai et al., 1987, Intl. J. Gyn. Path. 6:366–379.
Nuovo et al., 1991, Amer. J. Pathol. in press.
Frohman et al., 1988, Proc. Natl. Acad. Sci. USA 85:8998–9002.
Ward et al., 1989, Nature 341:544–546.
Newton et al., 1989, Nucl. Acids Res. 17:2503–2516.
Faloona et al., Abstract 1019, 6th International Conference on AIDS, Jun. 20–24, 1990, San Francisco, CA.
Chase and Williams, 1986, Ann. Rev. Biochem. 55:103–136.
Schwarz et al., 1990, Nucl. Acids Res. 18(4):1079.
Panaccio and Lew, 1991, Nucl. Acids Res. 19(5):1151.
Brayer and McPherson, 1984, Biochemistry 23:340–349.
Saito et al., 1988, Virology 167:653–656.
Citovsky et al., 1990, Cell 60:637–647.
Citovsky et al., 1989, Proc. Natl. Acad. Sci. US 86:1193–1197.
Prasad and Chiu, 1987, J. Mol. Biol. 193:579–584.
Science, vol. 240, issued 17 Jun. 1988, pp. 1661–1664.
Nucleic Acids Research, vol. 18, No. 4.
Fisher Scientific, 1983 Catalog, pp. 20–21.
Haase et al., "Amplification and detection of lentiviral DNA inside cells," Proceedings of the National Academy of Sciences, U.S.A., vol. 87, pp. 4971–4975. Jul. 1990.

*Primary Examiner*—W. Gary Jones
*Assistant Examiner*—Bradley L. Sisson
*Attorney, Agent, or Firm*—George M. Gould; Dennis P. Tramaloni; Stacey R. Sias

[57] ABSTRACT

Improvements to the in situ polymerase chain reaction (PCR), a process of in vitro enzymatic amplification of specific nucleic acid sequences within the cells where they originate, can be achieved by changing the way that the enzymatic reaction is started. Reaction initiation is delayed until the start of PCR thermal cycling, either by withholding a subset of PCR reagents from the cellular preparation until the preparation has been heated to 50° C. to 80° C., immediately before thermal cycling is begun, or by adding to the PCR reagents a single-stranded DNA binding protein which blocks reaction at temperatures below about 50° C. If the in situ PCR is performed on cellular preparations already attached to a microscope slide, thermal cycling also is facilitated by use of a thermal cycler sample block or compartment designed optimally to hold the microscope slide and any vapor barrier covering the slide.

24 Claims, No Drawings

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 1:

CAGGACCCAC AGGAGCGACC    20

( 2 ) INFORMATION FOR SEQ ID NO: 2:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 2:

TTACAGCTGG GTTTCTCTAC    20

( 2 ) INFORMATION FOR SEQ ID NO: 3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 3:

CCGGTCGATG TATGTCTTGT    20

( 2 ) INFORMATION FOR SEQ ID NO: 4:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 4:

ATCCCCTGTT TTTTTTCCA    20

( 2 ) INFORMATION FOR SEQ ID NO: 5:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 5:

GGTACGGGAT GTAATGGATG     20

( 2 ) INFORMATION FOR SEQ ID NO: 6:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 6:

CCACTTCCAC CACTATACTG     20

( 2 ) INFORMATION FOR SEQ ID NO: 7:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 7:

AGGTAGAAGG GCGCCATGAG     20

IN SITU POLYMERASE CHAIN REACTION

This application is a continuation of application Ser. No. 07/733,419, filed Jul. 23, 1991, now abandoned.

FIELD OF THE INVENTION

The present invention relates to novel compositions, devices, and methods for simplifying and improving the sensitivity and specificity of the in situ polymerase chain reaction, a method of amplifying and detecting specific nucleic acid sequences within individual cells, and will find broad use in the fields of cell biology, forensic science, and clinical, veterinary, and plant pathology.

BACKGROUND OF THE INVENTION

The polymerase chain reaction (PCR) is a method for increasing by many orders of magnitude the concentration of a specific nucleic acid sequence in a test sample. The PCR process is disclosed in U.S. Pat. Nos. 4,683,195; 4,683,202; and 4,965,188, each of which is incorporated herein by reference.

In PCR, a test sample believed to contain one or more targeted nucleic acid sequences is combined in a total volume of usually about 20 to 200 µl with the following reagents: an aqueous buffer, pH 8–9 at room temperature, usually also containing approximately 0.05 M KCl; all four common nucleoside triphosphates (e.g., for DNA polymerase, the four common dNTPs: dATP, dTTP, dCTP, and dGTP) at concentrations of approximately $10^{-5}$M to $10^{-3}$M; a magnesium compound, usually $MgCl_2$, usually at a concentration of about 1 to 5 mM; a polynucleotide polymerase, preferably a thermostable DNA polymerase, most preferably the DNA polymerase I from *Thermus aquaticus* (Taq polymerase and the Stoffel fragment of Taq polymerase are the subject of U.S. Pat. No. 4,889,818, incorporated herein by reference; the latter enzyme lacks the 5'→3' exonuclease activity of native Taq polymerase), usually at a concentration of $10^{-10}$ to $10^{-8}$M; and single-stranded oligonucleotide primers, usually 15 to 30 nucleotides long and usually composed of deoxyribonucleotides, containing base sequences which are Watson-Crick complementary to sequences on both strands of the target nucleic acid sequence(s). Each primer usually is present at a concentration of $10^{-7}$ to $10^{-5}$M; primers are synthesized by solid-phase methods well known in the art of nucleic acid chemistry.

In the simplest form, PCR requires two primers for each target sequence. These primers, when annealed to the opposing target strands, have their 3' ends directed toward one another's hybridization sites and separated by about 100 to 1,000 nucleotides (occasionally up to about 10,000 nucleotides). The polymerase catalyzes magnesium-dependent, template-directed extension of each primer from the 3' end of the primer, incorporating nucleoside monophosphates into the growing nucleic acid and releasing pyrophosphate.

This extension reaction continues until the polymerase reaches the 5' end of the template strand to which the extended primer was annealed, at which point the polymerase is free to bind to another primer-template duplex and catalyze extension of that primer molecule; the extension reaction also stops if the reaction mixture is heated to temperatures sufficient to separate the template from the extended primer before the enzyme has reached the 5' end of the template. After the enzyme has worked long enough to transform a large fraction of the primer-template duplexes into double-stranded nucleic acid, the latter can be denatured at high temperature, usually 90° to 100° C., to create two single-stranded polynucleotides, which, after cooling to a temperature where they can be annealed to new primer molecules, serve as templates for another round of enzyme-catalyzed primer extension. Because both DNA strands serve as template, each round of nucleic acid replication approximately doubles the concentration of the specific nucleic acid sequence defined at its ends by the two primer sequences. Therefore, the total concentration increase in the target nucleic acid sequence in a PCR amplification is by a factor of approximately $2^n$, where n is the number of completed thermal cycles between a high temperature where double-stranded DNA is denatured and a lower temperature or set of temperatures (40° to 75° C.) where primer-template annealing and primer extension occur.

Although one can move PCR reaction tubes manually back and forth between thermostated baths in the two temperature ranges, PCR most commonly is performed in an automated temperature-controlled machine, known as a "thermal cycler," in which a microprocessor is programmed to change the temperature of a heat-exchange block or bath containing reaction tubes back and forth among several specified temperatures for a specified number of cycles, holding at each temperature for a specified time, usually on the order of one-half to two minutes. Such a thermal cycler is commercially available from Perkin Elmer Cetus Instruments and described in the European Patent Publication No. 236,069 and U.S. patent application Ser. No. 670,545, filed Mar. 14, 1991, which is a continuation-in-part of Ser. No. 620,606, filed Nov. 29, 1990, both of which are incorporated herein by reference. The total cycle time is usually less than 10 minutes, and the total number of cycles is usually less than 40, so that a single, multi-cycle amplification, amplifying the targeted nucleic acid sequence $10^5$ to $10^{10}$ times, normally takes less than seven hours and often less than four hours.

The practical benefits of PCR nucleic acid amplification have been rapidly appreciated in the fields of genetics, molecular biology, cellular biology, clinical chemistry, forensic science, and analytical biochemistry, as described in the following review volumes and articles: Erlich (ed.), 1989, *PCR Technology*, Stockton Press (New York); Erlich et al. (eds.), 1989, *Polymerase Chain Reaction*, Cold Spring Harbor Press (Cold Spring Harbor, N.Y.); Innis et al., 1990, *PCR Protocols*, Academic Press (New York); and White et al, 1989, *Trends in Genetics* 5/6:185–189. PCR can replace a large fraction of molecular cloning and mutagenesis operations commonly performed in bacteria, having advantages of speed, simplicity, lower cost, and sometime increased safety. Furthermore, PCR permits the rapid and highly sensitive qualitative and even quantitative analysis of nucleic acid sequences, often with greatly increased safety because so much PCR product is made that nonisotopic detection modes suffice.

Despite rapid and broad adoption of PCR by a range of biological and chemical disciplines, PCR has sometimes suffered from the occurrence of side reactions which interfere with amplification of the specific target sequence or sequences. Many amplifications yield non specific side products differing in size and sequence from the sequence targeted by the primers used. Sometimes nonspecificity is caused by mis-priming, where primers have been annealed to non-target sequences, also present in the nucleic acid of the test sample similar to the target sequence. Although the genomic DNA commonly contained in PCR test samples has customarily been thought to be completely double-stranded, procedures used to prepare DNA for amplification appear to render that DNA, to a significant extent, single-stranded. Single-stranded DNA is especially susceptible to mis-priming if mixed with a complete set of PCR reagents at ambient or sub-ambient temperatures. Many PCR reagents also yield primer dimers or oligomers, double-stranded side products containing the sequences of several molecules joined end-to-end, the yield of which correlates negatively with the yield of amplified target sequence.

Recently several methodological modifications have improved PCR specificity and sensitivity significantly. In Hot Start™ PCR, complete mixing of PCR reagents and test sample is delayed until reactants have been heated to a temperature in the 50° C.–80° C. range, sufficient to minimize mis-priming and primer dimerization; thermal cycling is started immediately after mixing at elevated temperature. In manual Hot Start™ PCR, the operator heats the reaction tube, containing test sample and a subset of PCR reagents, to the elevated incubation temperature, opens each tube separately to add a small volume of liquid containing the missing reagent(s), and closes each tube before moving on to the next one. See Frohman et al., 1988, *Proc. Natl. Acad. Sci. USA* 85:8998–9002; Ward et al., 1989, *Nature* 341:544–546; Newton et al., 1989, *Nucl. Acids Res.* 17:2503–2516; and Faloona et al., Abstract 1019, 6th International Conference on AIDS, June 20–24, 1990, San Francisco, Calif. More recently, Hot Start™ PCR was rendered more convenient and precise by (1) replacement of the conventional mineral oil vapor barrier by a layer of wax melting in the 50° C. to 80° C. range, (2) assembly of reaction tubes such that before thermal cycling, PCR reactants are grouped into subsets separated by a solid wax layer, and (3) convective mixture of all reactants during the first heating step of thermal cycling after the solid wax melts into a lighter-than-water oil. Such wax-mediated, Hot Start™ PCR is the subject of U.S. patent application Ser. No. 481,501, filed Feb. 19, 1990, now abandoned in favor of continuation application U.S. Ser. No. 07/890,300, filed May 27, 1992, incorporated herein by reference.

Alternatively, nonspecific amplified nucleic acid resulting from primer dimerization and mis-priming while completely mixed PCR reactants stand at room temperature before thermal cycling can be destroyed by an enzymatic restriction process described in PCT U.S. patent application Ser. No. 91/05210 filed Jul. 23, 1991, which published as PCT Patent Publication No. WO 92/01814 on Feb. 6, 1992, which is a continuation-in-part of U.S. Ser. No. 609,157, filed Nov. 2, 1990, now abandoned which is a continuation-in-part of U.S. Ser. No. 557,517, filed Jul. 24, 1990, now abandoned each of which is incorporated herein by reference. To perform such restriction, one of the conventional four dNTPs is replaced by a structural analogue which is incorporated into all amplified nucleic acid by the PCR polymerase. Also included in the reaction mixture is an enzyme which digests nucleic acid at (and only at) positions which contain the structural analogue; this enzyme must be active only at temperatures below about 50° C., so that it does not damage amplified nucleic acid during thermal cycling at higher temperatures. Preferably the restriction enzyme is permanently inactivated during thermal cycling, so that it cannot damage amplified nucleic acid if the latter is stored for any significant period of time at room temperature after amplification and before analysis. The most practical restriction enzymes are glycosidases which cleave from the polynucleotide phosphodiester backbone the unconventional nucleic acid base introduced by the dNTP analogue. The resulting abasic sites experience cleavage of the polynucleotide phosphodiester backbone upon heating. This restriction process has been integrated practically with PCR by replacing dTTP with dUTP and by incorporating in the reaction mixture the enzyme uracil-N-glycosidase.

A chemical variant of the Hot Start™ process incorporates into the PCR reagent mixture a single-stranded DNA binding protein (SSB) at a concentration sufficient to bind a significant fraction of the single-stranded DNA present before thermal cycling is started. This ssDNA comprises minimally the primers, the concentrations of which are well known by the operator, and may also include slight or considerable amounts of the test sample DNA, depending on whether the latter has been prepared in a way which might denature it. During thermal cycling, the binding of the SSB to primers and single-stranded template strands formed by PCR product denaturation must be weak enough not to interfere with primer-template annealing and enzymatic primer extension. Before thermal cycling, while reactants stand together at room temperature, SSB binding to the primers and any single-stranded regions of test sample DNA must be strong enough to block mis-priming and primer dimerization. Two heavily studied SSBs (Chase and Williams, 1986, *Ann. Rev. Biochem.* 55:103–136) are commercially available and have been used with PCR: gene 32 protein from the bacteriophage T4 and the 19 kilodalton SSB from *E. coli* (19 kda is the subunit size; the normal active species is a tetramer). SSB is the major active ingredient of Perfect Match™ polymerase enhancer, a mixture of *E. coli* SSB and bovine serum albumin sold by Stratagene (San Diego, Calif.) for the purpose of increasing PCR specificity and yield. Bacteriophage gene 32 protein has been included in PCR mixtures to improve amplification of long targets (Schwarz et al., 1990, *Nucl. Acids Res.* 18:1079) and to relieve polymerase inhibition by blood in the test sample (Panaccio and Lew, 1991, *Nucl. Acids Res.* 19:1151). However, essentially all organisms possess SSBs with compositions unique to each organism. Other SSBs which have been characterized biochemically include one from a filamentous bacteriophage (Brayer and McPherson, 1984, *Biochemistry.* 23:340–349), a family of sequence-homologous proteins from plant virus (Saito et al., 1988, *Virology* 167:653–656, and Citovsky etal., 1990, *Cell* 60:637–647), and one from *Agrobacterium tumefaciens* (Citovsky et al., 1989, *Proc. Natl. Acad. Sci. USA* 86:1193–1197). SSBs possess enough structural similarity to suggest that DNA binding is associated with a consensus structure of alternating aromatic amino acids (phenylalanine, tyrosine, and tryptophan) and charged amino acids (glutamate, aspartate, lysine, and arginine) (Prasad and Chiu, 1987, *J. Mol. Biol.* 193:579–584) such that artificial polypeptides might be created which function as well as the biological SSBs in improving PCR specificity and yield. In addition, enough is known about SSB structure and function to suggest ways to improve function by genetic engineering.

Although the three basic tactics of PCR specificity enhancement (Hot Start™ methods, amplified DNA restriction, and SSB addition to the reaction mixture) each can serve alone to improve specific amplification, combinations of the three approaches may have special benefits. For example, whereas Hot Start™ methods block only that nonspecificity resulting from reactant incubation at ambient temperature before cycling is started, SSB s may reduce mis-priming which arises during thermal cycling. On the other hand, SSB used without a manual or wax-mediated Hot Start™ process occasionally will trigger massive primer dimerization which interferes with specific amplification. The combination of the two methods optimally reduces mis-priming and primer dimerization.

The preceding background art has dealt with conventional PCR, wherein test sample nucleic acids are extracted from a biological source in a way which destroys target sequence association with individual cells or subcellular structures. So-called in situ nucleic acid hybridization methods have evolved to detect target sequences in the cells or organelles where they originated (for a review of the field, see Nagai et 1987, *Intl. J. Gyn. Path.* 6:366–379). Typically, in situ hybridization entails (1) preparation of a histochemical section or cytochemical smear, chemically fixed (e.g., with formaldehyde) to stabilize proteinaceous subcellular structures and attached to a microscope slide, (2) chemical denaturation of the nucleic acid in the cellular preparation, (3) annealing of a tagged nucleic acid probe to a complementary target sequence in the denatured cellular DNA, and (4) localized detection of the tag annealed to target, usually by microscopic examination of immobilized nonisotopic (absorbance or fluorescence staining) or isotopic (autoradiographic) signals directly or indirectly generated by the probe tag. However, conventional in situ hybridization is not very sensitive, generally requiring tens to hundreds of copies of the target nucleic acid per cell in order to score the presence of target sequence in that cell.

Recently, the sensitivity enhancement associated with PCR amplification of target sequence has been combined with the target localization of in situ hybridization to create in situ PCR, wherein PCR is performed within chemically fixed cells, before (Haase et al., 1990, *Proc. Natl. Acad. Sci. USA* 87:4971–4975, incorporated herein by reference) or after (Nuovo et al., 1991, *Amer. J. Pathol.* in press, incorporated herein by reference) the fixed cells have been attached to a microscope slide; the amplified nucleic acid is located by microscopic examination of autoradiographs following isotopically tagged probing (Haase et al., supra) or stained patterns directly deposited on the microscope slide following enzyme-linked detection of biotin-tagged probes (Nuovo et al., supra). The cells may be suspended (Haase et al., Supra) or may be part of a tissue section (Nuovo et al., supra) during in situ amplification.

In situ PCR requires a delicate balance between two opposite requirements of PCR in a cellular preparation: the cell and subcellular (e.g., nuclear) membranes must be permeabilized sufficiently to allow externally applied PCR reagents to reach the target nucleic acid, yet must remain sufficiently intact and nonporous to retard diffusion of amplified nucleic acid out of the cells or subcellular compartments where it is made. In addition, the amplified nucleic acid must be sufficiently concentrated within its compartment to give a microscopically visible signal, yet remain sufficiently dilute that it does not reanneal between the denaturation and probe-annealing steps. Haase et al., supra, relied on paraformaldehyde fixation of cells to have created sufficient but not excessive permeability. Nuovo et al., supra, also employed a single, commercially available, proteinase treatment to improve permeability.

Both Haase et al., supra, and Nuovo et al., supra, used a series of PCR primer pairs to specify a series of overlapping target sequences within the genome of the targeted organism to improve retention of amplified target nucleic acid within the cellular compartment where it was made. The resulting PCR product was expected to be so large (greater than 1,000 base pairs) that its diffusion from site of origin should be greatly retarded. However, the use of multiple primer pairs severely reduces the practicality of in situ PCR, not just because of the expense associated with producing so many synthetic oligonucleotides, but even more seriously because many PCR target organisms, especially pathogenic virus, are so genetically plastic that it is hard to find even a few short sequences which are sufficiently invariant to make good primer and probe sites. Other important target sequences, such as activated oncogenes, inactivated tumor suppressor genes, and oncogenic chromosomal translocations, involve somatic point mutations and chromosomal rearrangements which can be distinguished from the parental sequence if relatively short PCR products are amplified from single primer pairs. Multiple primer pairs and long structures would frustrate attainment of the specificity often needed to distinguish cancerous cells from their normal neighbors. Multiple primer pairs jeopardize PCR in a different way as well; they promote primer dimerization and mis-priming, reducing sensitivity and specificity and increasing the likelihood of false-negative results because nonspecific amplification radically reduces the yield of amplified target sequence. Reinforcing the tendency of multiple primer pairs to enhance nonspecific amplification are the rather high primer concentrations preferred for in situ PCR (Nuovo et al., supra).

One useful variant of conventional PCR detects target RNA sequences in test samples by creating complementary DNA (cDNA) sequences with the catalytic mediation of added reverse transcriptase; the cDNA then is subjected to standard PCR amplification (Kawasaki et al., 1988, *Proc. Natl. Acad. Sci. USA* 85(15):5698, and Rappolee et al., 1989, *J. Cell. Biochem.* 39:1–11). Recently, such RNA PCR has been streamlined by using a thermostable DNA polymerase which, depending on exact chemical conditions, also shows strong reverse transcriptase activity. This enzyme and its optimized application to RNA PCR are subject of PCT U.S. patent application Ser. No. US90/07641, filed Dec. 21, 1990, incorporated herein by reference. Adaptation of in situ PCR to RNA targets will realize the full potential of the method to differentiate among neighboring cells in a histochemical or cytochemical preparation with respect to somatic mutation, pathogenic infection, oncogenic transformation, immune competence and specificity, state of differentiation, developmental origin, genetic mosaicism, cytokine expression, and other characteristics useful for understanding both normal and pathological conditions in eukaryotic organisms.

The present invention increases the convenience, sensitivity, and specificity of in situ PCR, also eliminating any need for multiple primer pairs to detect a single target sequence. In doing so, it also allows in situ PCR to discriminate among alleles and increases the practicality of in situ PCR analysis of RNA targets.

SUMMARY OF THE INVENTION

In a first aspect, the invention provides an improved method of in situ polymerase chain reaction (PCR) with increased amplification specificity and sensitivity. This improvement involves withholding at least one PCR reagent from a preparation comprising fixed cells and PCR reagents until the preparation has been heated to a temperature, in the approximate range of 50° C. to 80° C., where nonspecific reactions of the nucleic acid polymerase are disfavored. The method applies equally whether nucleic acid, amplification is performed before or after the fixed cells have been attached to a microscope slide.

In a second aspect, the improved in situ PCR method relates to the better specificity and sensitivity that result by including in the reaction mixture a single-stranded DNA binding protein (SSB) at a concentration which interferes with nonspecific polymerase reactions without blocking specific target amplification. A variety of naturally occurring, genetically engineered, or totally synthetic polypeptides with SSB activity can benefit in situ PCR. This second aspect also is independent of the temporal order of nucleic acid amplification and cell attachment to slides.

In a third aspect, the improved in situ PCR method relates to the better specificity and sensitivity that result by including dUTP and UNG, or another modified nucleotide and corresponding glycosylase, in the reaction mixture.

In a final aspect, the invention relates to modified thermal cyclers used to automate PCR amplification, wherein the sample compartment used to transfer heat rapidly to and from the reaction holds microscope slides. In one embodiment, the sample compartment comprises a metal block which has a horizontal flat surface dimensioned to hold one or several microscope slides with their largest dimensions oriented horizontally. The flat surface may lie at the bottom of a well suitable for holding a shallow mineral oil vapor barrier which prevents drying of the in situ PCR preparation during thermal cycling. In another embodiment, the compartment comprises a metal block containing one or more slots which substantially and closely enclose microscope slides with their largest dimensions oriented in an approximately vertical plane. Such orientation substantially increases the number of slides which can be analyzed at one time. In a third embodiment, the compartment holds a moving heat-transfer fluid and contains holders for securing microscope slides in the fluid flow. The third embodiment also comprises plastic envelopes which encase the microscope slides and protect them from desiccation or PCR reagent wash-out.

DETAILED DESCRIPTION OF THE INVENTION

The first three aspects of the invention improve the specificity and sensitivity of in situ PCR; they reduce the chance of false negative results because even cells containing only a single copy of target nucleic acid sequence can confidently detected. The increased specificity simplifies the detection of amplified nucleic acid. Whereas in situ nucleic acid analysis traditionally has required annealing of tagged probe nucleic acid containing sequence complementary to the target sequence, high amplification specificity allows confident detection of tagged primers which have been incorporated into longer nucleic acid, with decreased concern for false positive results which might arise from primer incorporation into nonspecifically amplified nucleic acid. Therefore, an additional probing step is no longer needed but still can be used. The increased sensitivity also simplifies detection of amplified nucleic acid after in situ PCR, by generating so much analyte that nonisotopic signals can replace autoradiographically recorded isotopic signals. Absorbance, fluorescence, and chemiluminescence signals are faster, simpler, and safer to record than is radioactive decay. Adoption of nonisotopic detection should greatly increase the appeal of in situ PCR to clinical pathologists and other practitioners of routine analysis (as opposed to biological and medical research).

The first three aspects of the invention also greatly increase the practicality and generality of in situ PCR by eliminating the need for multiple primer pairs for sensitive detection of a single target sequence. Quite apart from the expense, multiple primer pairs are hard to apply to highly polymorphic target organisms, like many retrovirus, or to allele-specific amplification such as is required for PCR detection of many oncogenic somatic mutations. Now that single primer pairs suffice for in situ PCR, the method will have the same breadth of application as conventional PCR. Such special adaptions as multiplex PCR, degenerate priming, nested priming, allele-specific amplification, one-sided PCR, and RNA PCR can be tried in situ with increased confidence in method transfer.

The second aspect of the invention is also a significant improvement. Hot Start™ methods block only pre-amplification side reactions which yield nonspecific products; SSBs also appear to reduce mis-priming which occurs during thermal cycling. Therefore, SSBs more effectively reduce nonspecific amplification. Two, inclusion of an SSB in the PCR reagent mixture eliminates the need to perform a manual Hot Start™ procedure, which requires some operator skill to effect a closely timed addition of the missing PCR reagent without damaging or desiccating the in situ PCR preparation. A method where all components of the assay are assembled at room temperature and covered with a vapor barrier before heating is begun is more reliable than one which requires manipulation of hot materials and vapor barrier addition to a hot system.

By facilitating routine application of in situ PCR, the first two aspects of the invention extend ultra-sensitive nucleic acid detection to new markets and practical problems, such as are presented by clinical, veterinary, and plant pathology. These professional fields often rely on information regarding analyte location in biological samples to make critical judgments; conventional PCR does not easily yield that information. Furthermore in situ PCR is practically immune to the creation of false-positive results by contamination of reactions with amplified target from previous reactions, because the analyte shows subcellular localization, usually in the nucleus. In addition, multiple staining, for example, for cell-surface antigens, permits disease diagnosis and prognosis based on infection rates of cellular subpopulations. In situ PCR applied to blood or biopsy samples from patients believed to be infected by a lymphotrophic retrovirus, such as HIV-1, should yield valuable prognosis information such as the fraction of CD4 (surface antigen) plus cells carrying integrated viral genomes or vital particles.

The instruments of modified heat blocks of this invention will increase the speed and reliability of in Silo PCR performed on microscope slides by accelerating and rendering more uniform the heat transfer which occurs during thermal cycling. Nuovo et at., supra, placed the microscope slide in a foil boat designed to hold the mineral oil vapor barrier which rested on top of a conventional thermal cycler sample block. Because such sample blocks contain rows of Wells designed to hold the microcentrifuge tubes in which conventional PCR is performed, they reduce the heat transfer rate from the maximum possible value; the microscope slide does not contact the sample block directly, and a large fraction of the bottom of the foil boat contacts the poorly conducting air in the sample wells rather than the metal of the sample block.

To promote understanding of the invention, definitions are provided below for the following terms.

"PCR" refers to a process of amplifying one or more specific nucleic acid sequences, wherein (1) oligonucleotide primers which determine the ends of the sequences to be amplified are annealed to single-stranded nucleic acid in a test sample, (2) a nucleic acid polymerase extends the 3' ends of the annealed primers to create a nucleic acid strand complementary in sequence to the nucleic acid to which the primers were annealed, (3) the resulting double-stranded nucleic acid is denatured to yield two single-stranded nucleic acids, and (4) the processes of primer annealing, primer extension, and product denaturation are repeated enough times to generate easily identified and measured amounts of the sequences defined by the primers. Practical control of the sequential annealing, extension, and denaturation steps is exerted by varying the temperature of the reaction container, normally in a repeating cyclical manner. Annealing and extension occur optimally in the 40° C. to 80° C. temperature range (exact value depending on primer concentrations and sequences), whereas denaturation requires temperatures in the 80° C. to 100° C. range (exact value depending on target sequence and concentration).

Such "thermal cycling" commonly is automated by a "thermal cycler," an instrument which rapidly (on the time scale of one to several minutes) heats and cools a "sample compartment," a partly or completely enclosed container holding the vessel in which nucleic acid amplification occurs and the heat-transfer medium directly contacting the PCR vessel. Most commonly the sample compartment is a "sample block," normally manufactured out of metal, preferably aluminum. Conventional sample blocks contain wells designed to fit tightly the plastic microcentrifuge tubes in which PCR amplification nounally is performed. The sample block of the present invention replaces some or all of these conical wells with flat surfaces or slots designed to optimize heating and cooling of microscope slides. Less commonly, the sample compartment is a chamber through which a hot or cold heat-transfer fluid, such as air or water, moves past reaction tubes bathed by the fluid.

"PCR reagents" refers to the chemicals, apart from test sample nucleic acid, needed to make nucleic acid amplification work. They consist of five classes of components: (1) an aqueous buffer, (2) a water-soluble magnesium salt, (3) at least four deoxyribonucleoside triphosphates (dNTPs), (4) oligonucleotide primers (normally two for each target sequence, with sequences which define the 5' ends of the two complementary strands of the double-stranded target sequence), and (5) a polynucleotide polymerase, preferably a DNA polymerase, most preferably a thermostable DNA polymerase, which can tolerate temperatures between 90° C. and 100° C. for a total elapsed time of at least 10 minutes without losing more than about half of its activity.

The four conventional dNTPs are thymidine triphosphate (dTTP), deoxyadenosine triphosphate (dATP), deoxycytidine triphosphate (dCTP), and deoxyguanosine triphosphate (dGTP). They can be augmented or sometimes replaced by dNTPs containing base analogues which Watson-Crick base-pair like the conventional four bases. Examples of such analogues include deoxyuridine triphosphate (dUTP) and dUTP carrying molecular tags such as biotin and digoxigenin, covalently attached to the uracil base via spacer arms.

Whereas a "complete set" of PCR reagents refers to the entire combination of essential reactants except test sample nucleic acid, a "subset" of PCR reagents lacks at least one of the essential reagents other than the aqueous buffer. The "complement" or "complementary subset" to a first PCR reagent subset consists of all reagents missing from the first subset. PCR "reactants" refers to the PCR reagents plus text sample nucleic acid.

"Hot Start™ PCR" refers to PCR amplification in which a subset of reagents is kept separate from its complement and the test sample until the latter components have been heated to a temperature between about 50° C. and about 80° C., hot enough to minimize nonspecific polymerase activity. After all PCR reactants have been mixed, thermal cycling is begun, with reaction temperature controlled so that it never drops below about 50° C. until amplification is completed.

"Fixed cells" refers to a sample of biological cells which has been chemically treated to strengthen cellular structures, particularly membranes, against disruption by solvent changes, temperature changes, mechanical stresses, and drying. Cells may be fixed either in suspension or while contained in a sample of tissue, such as might be obtained during autopsy, biopsy, or surgery. Cell fixatives generally are chemicals which crosslink the protein constituents of cellular structures, most commonly by reacting with protein amino groups. Preferred fixatives are buffered formalin, 95% ethanol, formaldehyde, paraformaldehyde, or glutaraldehyde. Fixed cells also may be treated with proteinases, enzymes which digest proteins, or with surfactants or organic solvents which dissolve membrane lipids, in order to increase the permeability of fixed cell membranes to PCR reagents. Such treatments must follow fixation to assure that membrane structures do not completely fall apart when the lipids are removed or the proteins are partially cleaved. Protease treatment is preferred following fixation for more than one hour and is less preferred following shorter fixation intervals. For example, a ten-minute fixation in buffered formalin, without protease treatment, is standard after suspended cells (e.g., from blood) have been deposited centrifugally on a slide by cytospin procedures standard in the cytochemical art.

"Histochemical section" refers to a solid sample of biological tissue which has been frozen or chemically fixed and hardened by embedding in a wax or a plastic, sliced into a thin sheet, generally several microns thick, and attached to a microscope slide.

"Cytochemical smear" refers to a suspension of cells, such as blood cells, which has been chemically fixed and attached to a microscope slide.

"In situ PCR" refers to PCR amplification performed in fixed cells, such that specific amplified nucleic acid is substantially contained within the cell or subcellular structure which originally contained the target nucleic acid sequence subjected to specific amplification. The cells may be in aqueous suspension or may be part of a histochemical section or cytochemical smear. Preferably the cells will have been rendered permeable to PCR reagents by proteinase digestion or by lipid extraction with surfactant or organic solvent. An "in situ PCR preparation" consists of a combination of fixed cells with a subset or complete set of PCR reagents.

"Vapor barrier" refers to an organic material, in which water is insoluble, which covers a PCR reaction or preparation in a way which substantially reduces water loss to the atmosphere during thermal cycling. Preferred vapor barrier materials are liquid hydrocarbons such as mineral oil, or paraffin oil, although some synthetic organic polymers, such as fluorocarbons and silicon rubber, also may serve as effective PCR vapor barriers. Waxes which are solid at temperatures below about 50° C. and liquid at higher temperatures also make convenient vapor barriers. The vapor barrier may be a thin plastic film, fabricated into an envelope completely enclosing the PCR or glued to a microscope slide carrying an in situ PCR in such a way as to isolate the reaction from the atmosphere.

"Single-stranded DNA binding protein" (SSB) refers to a polypeptide which binds to single-stranded DNA more tightly than to double-stranded DNA. Naturally occurring SSBs include the bacteriophage T4 gene 32 protein, the filamentous bacteriophage gene 5 protein, the SSB from E.

*coli* with a subunit molecular weight of 19 kilodaltons, the 30 kilodalton movement proteins of tobamoviruses, and *Agrobacterium tumefaciens* vir E2 protein.

"Detection" of PCR-amplified nucleic acid refers to the process of observing, locating, or quantitating an analytical signal which is inferred to be specifically associated with the product of PCR amplification, as distinguished from PCR reactants. The analytical signal can result from visible or ultraviolet absorbance or fluorescence, chemiluminescence, or the photographic or autoradiographic image of absorbance, fluorescence, chemiluminescence, or ionizing radiation. Detection of in situ PCR products involves microscopic observation or recording of such signals. The signal derives directly or indirectly from a molecular "tag" attached to a PCR primer or dNTP or to a nucleic acid probe, which tag may be a radioactive atom, a chromophore, a fluorophore, a chemiluminescent reagent, an enzyme capable of generating a colored, fluorescent, or chemiluminescent product, or a binding moiety capable of reaction with another molecule or particle which directly carries or catalytically generates the analytical signal. Common binding moieties are biotin, which binds tightly to streptavidin or avidin, digoxigenin, which binds tightly to anti-digoxigenin antibodies, and fluorescein, which binds tightly to anti-fluorescein antibodies. The avidin, streptavidin, and antibodies are easily attached to chromophores, fluorophores, radioactive atoms, and enzymes capable of generating colored, fluorescent, or chemiluminescent signals.

"Nucleic acid probe" refers to an oligonucleotide or polynucleotide containing a sequence complementary to part or all of the PCR target sequence, also containing a tag which can be used to locate cells in an in situ PCR preparation which retains the tag after mixing with nucleic acid probe under solvent and temperature conditions which promote probe annealing to specifically amplified nucleic acid.

A preferred mode of fixing cell samples for in situ PCR according to the present invention is to incubate them in 10% formalin, 0.1 M Na phosphate, pH 7.0, for a period of 10 minutes to 24 hours at room temperature. The cells may be a suspension, as would be obtained from blood or a blood fraction such as buffy coat, or may be a solid tissue, as would be obtained from biopsy, autopsy, or surgical procedures well known in the art of clinical pathology. If PCR is to be performed in cell suspension, suspended cells preferably are centrifuged after formalin fixation, resuspended in phosphate-buffered saline, and re-centrifuged to remove the fixative. The washed, pelleted cells may be resuspended in PCR buffer and added directly to a PCR tube. If PCR is to be performed on a microscope slide, suspended cells preferably are deposited on the slide by cytospin, fixed 10 minutes in buffered formalin, washed 1 minute in water, and washed 1 minute in 95% ethanol. Alternatively, suspended cells can be pelleted in a centrifuge tube and the pellet can be embedded in paraffin and treated like a tissue specimen. Tissue samples may be processed further and then embedded in paraffin and reduced to serial 4–5 μm sections by microtome procedures standard in the art of clinical pathology. Histochemical sections are placed directly on a microscope slide. In either case, the slide preferably will have been treated with 2% 3-aminopropyltriethoxysilane in acetone and air dried. After smears or sections have been applied to slides, the slides are heated at about 60° C. for about 1 hour. Paraffin-embedded sections can be deparaffinized by 2 serial 5 minute washes in xylene and 2 serial 5 minute washes in 100% ethanol, all washes occurring at room temperature with gentle agitation.

Choosing PCR primer sequences, preparing PCR reagents and reaction mixtures, and designing and running PCR reactions are well known procedures in the PCR art. In the event that nucleic acid amplification is performed on suspended cells in a standard PCR tube, the cells are treated like any conventional PCR test sample: diluted into reaction mixture shortly before amplification is started, at a total cell number ranging from approximately 100 to approximately $10^6$. For carrying out the first aspect of the invention in a reaction tube, the only change from conventional PCR practice is that at least one reagent, preferably enzyme but quite possibly primers, dNTPs, or $MgCl_2$, is omitted from the reaction mixture. After 50 to 100 μl of mineral oil have been added to the reaction tube, the tube is placed in a thermal cycler, many versions of which are commercially available from suppliers such as Perkin Elmer Cetus Instruments, and heated to a temperature between about 50° C. and about 80° C., preferably between 70° C. and 80° C. While the tube is held at that temperature, the missing reagent is delivered beneath the vapor barrier with a standard manual sampler, preferably in a 5 to 15 μl volume of PCR buffer. If multiple samples are amplified simultaneously in different tubes, a fresh sampler tip is used to add the missing reagent(s) to each tube, to prevent cross-contamination. After all tubes have been prepared and capped, the standard three-temperature thermal cycle program of denaturation, annealing, and extension for approximately 10 to 40 cycles is performed under thermal cycler microprocessor control. Alternatively, and often preferably, a series of two-temperature cycles can be run wherein annealing and extension are performed at a single temperature, normally optimized for stringent annealing of primer to template. Because reaction rates may be somewhat retarded with cellular preparations as compared to cell-free nucleic acids, it may be necessary to increase the durations of the denaturation, anneal, extend, or anneal-extend cycle segments as much as several-fold from values standard when the test sample contains cell-free nucleic acid. This adjustment easily is performed by trial and error, looking for conditions which maximize the intensity of the signal seen during amplified nucleic acid detection or which minimize the number of cycles needed to reach a given signal intensity. A similar optimization procedure can be used for $MgCl_2$, dNTP, primer, and enzyme concentrations in the reaction mixture; these parameters often show different optima for different targets, and also may be affected when amplification occurs within fixed cells.

For carrying out the second aspect of the invention in a reaction tube, several changes from the preferred mode just described are needed. There is no need to carry out the manual Hot Start™ procedure described above; all reactants can be mixed and the vapor barrier added at room temperature before thermal cycling is started. However, it is important that reagents be mixed in an order such that the SSB not be added last. Preferably, SSB will be pre-mixed with primers and the two reagents added together to the remaining reactants. The optimal quantity of SSB will vary with the identity of the SSB and with the quantity of single-stranded DNA in each reaction, and can be determined by trial and error according to the criteria given above for optimizing thermal cycle parameters. Because cellular preparations normally should contain little single-stranded DNA, the amount of primers in a reaction permits approximation of the optimal quantity of SSB, in the following way: (1) calculate the total moles of all primers from the number of primers used, their concentrations, and the reaction volume; (2) divide the average primer length by the known value for the footprint of the particular SSB used and round off to the nearest integer; (3) multiply this integer times the total moles of primer to get the total moles of SSB needed to react with all of the primer; and (4) add an amount of SSB equal to 0.5 to 2 times the calculated minimal amount of SSB. Further adjustment can be done by trial and error. The SSB footprint is the number of nucleotides occupying one SSB binding site. The following approximate SSB footprints have been reported in the research literature: 8 nucleotides for bacteriophage T4 gene 32 protein; between 33 and 65 nucleotides per *E. coli* SSB tetramer; 5 nucleotides per filamentous phage gene 5 protein monomer; 4 to 7 nucleotides per 30 kilodalton tobamovirus movement protein monomer; 30 nucleotides per 64 kilodalton *Agrobacterium tumefaciens* vir E2 protein monomer.

Whether the first, second, or third aspect of the invention is applied to fixed cells suspended in a standard PCR tube, the preferred post-PCR treatment required for microscopic analysis is the same. The cells are pelleted and washed once in phosphate-buffered saline before deposition on organosilane-treated slides as described above, either as a smear or as a microtome section through a paraffin-embedded pellet. Heating at 60° C. for one hour improves cell adherence to the slide.

In the event that the first or second aspect of the invention is applied to histochemical sections or cytochemical smears attached to microscope slides, amplification procedures differ somewhat from those described above for reactions in PCR tubes. A preferred mode of effecting the first aspect of the invention on microscope slides is to cover the section or smear with approximately 5 to 10 µl of a PCR reagent mixture lacking at least one reagent, such as enzyme. Then a plastic cover slip is placed over this preparation, the microscope slide is placed inside an aluminum foil boat, about 5 to 10 mm deep, the bottom of which is slightly larger than the slide, and the boat is placed on a metal thermal cycler sample block. After the sample block is brought to about 80° C. and held at that temperature, the cover slip is lifted and 2 to 10 µl of PCR buffer containing the missing reagent(s) are distributed across the surface of the reagent mixture. The cover slip is replaced before the in situ PCR preparation dries out, a drop of nail polish is applied to one corner of the cover slip to anchor it to the slide, and the slide is covered with enough mineral oil to assure that all cover slips, including their edges, are protected from the atmosphere. Preferably the oil has been pre-heated, so that its addition does not transiently reduce the temperature of the in situ PCR preparation. Then a standard two-temperature or three-temperature thermal cycle is run for about 40 cycles. As above, cycle parameters, number of cycles, and PCR reagent concentrations may need optimization to compensate for the abnormal heating and cooling kinetics of the oil-covered microscope slide and for possible reaction rate changes caused by the cellular nature of the test sample. After amplification, the mineral oil is removed from the slide with an organic solvent such as xylene, and the slides are dried with 100% ethanol or a graded series of ethanol concentrations. The oil-free preparation is incubated for approximately 15 minutes at about 50° C. in 0.15M NaCl, 0.015 M Na citrate, pH 7.0 to remove unreacted PCR reagents. This step is most useful if primers or dNTPs have been tagged.

A preferred mode of effecting the second aspect of the invention on microscope slides is to follow the procedure recommended above for the first aspect, with a few changes. The manual Hot Start™ method is not necessary, although it can still be used. A quantity of an SSB is added to the reagent mixture which is estimated to suffice to bind all of the single-stranded DNA in the in situ PCR preparation. This estimation is performed as described above for in situ PCR performed in reaction tubes. As before, it is important that the SSB not be the last reagent added; preferably it is pre-mixed with primers, the major form of single-stranded DNA. If the manual Hot Start™ method is not used, the entire preparation is assembled, covered with a plastic cover slip (which is anchored to the microscope slide with a drop of nail polish), placed in the foil boat, and covered with mineral oil at room temperature; a normal series of thermal cycles is used, without holding initially at 70° C. to 80° C. Post-PCR oil removal and preparation drying are as above.

The detection phase of in situ PCR is performed the same way, whether following the first, second, or the third aspect of the invention and whether PCR is performed in a reaction tube or on a microscope slide. There are two basic detection strategies. The first strategy involves tagging either the PCR primers or at least one of the dNTPs with a radioisotope or with a binding moiety such as biotin, digoxigenin, or fluorescein, or with another fluorophore. In this case, tag incorporated into amplified nucleic acid can be analyzed directly, provided that the unreacted tagged reagent has been washed out post-PCR and provided that the washing and drying procedure has not mobilized the amplified nucleic acid from its point of synthesis. The analytical validity of this simple detection strategy requires that the invention has increased in situ PCR specificity sufficiently that negligible nonspecific products have been made which are large enough to resist washing from the preparation. To test and validate this consequence of the first three aspects of the invention, appropriate control reactions can be performed. The logically most compelling control reaction is to perform the procedure on cells known to lack the target sequence; validation of the simplified detection strategy requires that no signal be generated in the control cells. Often such control cells are present in a histochemical or cytochemical preparation, so that the standard analysis contains its own control. A less compelling control is to use primers which differ sufficiently from the optimal primers for the target sequence that they will not amplify the target sequence under the specified annealing and extension conditions.

The second strategy involves detecting amplified nucleic acid by in situ hybridization to a tagged nucleic acid probe: an oligonucleotide or polynucleotide with a sequence complementary to at least part of the amplified nucleic acid sequences (preferably excluding the primer sequences). In situ hybridization, well known in the histochemical and cytochemical art, has four basic steps: denaturation of DNA in the test sample, annealing of probe to test sample nucleic acid under stringent conditions, wash of the microscope slide with a solvent under stringent conditions to remove unhybridized probe, and detection of the probe which has been retained on the slide.

Regardless of which detection strategy is used, the methods for observing and recording the presence and location of tag on the microscope slide are the same. If the tag is a radioisotope (preferably a strong beta radiation-emitter, such as $^{32}$P or $^{125}$I), the microscope slide is coated with nuclear track emulsion such as NTB-2 from Eastman Kodak Co (Rochester, N.Y.), incubated at 4° C. for an interval determined by trial and error, and developed by standard methods to leave microscopically detectable silver grains in the vicinity of immobilized tags. Procedures for $^{125}$I tagging probe or PCR product are described by Haase et al., supra, incorporated herein by reference. If the tag is a fluorophore, it may be observed directly in a fluorescence microscope with excitation and emission filters optimized for the particular fluorophore. This detection method is particularly suitable for multiplex in situ PCR with different primer pairs for different target nucleic acid sequences. Either different fluorophores can be attached to primers of different specificity, or different fluorophores can be attached to probes of different specificity. Methods of attaching fluorophores to oligonucleotides and polynucleotides, preferably at their 5' ends, are well known in the nucleic acid chemistry and PCR arts. If the tag is a binding moiety such as biotin or digoxigenin, it is incorporated directly into PCR product (via primers or dNTPs) or into probes by essentially the same methods used to attach other tags. However, in this case, signal generation requires additional detection steps. Preferably, the microscope slide is incubated in buffered aqueous solvent containing a covalent conjugate of a detection enzyme and a binding protein specific for the tag (avidin or streptavidin for biotin, an anti-digoxigenin antibody for digoxigenin, an anti-fluorescein antibody for fluorescein). The preferred detection enzyme is horseradish peroxidase or alkaline phosphatase. After unbound enzyme conjugate is removed by washing in a buffered aqueous solvent, the microscope slide is immersed in a solution containing a chromogenic substrate for the enzyme used. After an insoluble dye, product of the enzyme reaction, has been deposited at points on the microscope slide where enzyme conjugate has been bound, unreacted substrate is washed away in water or buffered aqueous solvent to prevent the buildup of nonspecific background stain over time. The preferred chromogenic substrates which generate insoluble products are well known in the histochemical and cytochemical art, as are the methods for staining and for enzyme conjugate incubation and washing. The substrates and enzyme conjugates are commercially available from a wide variety of sources well known to histochemists and cytochemists.

A preferred companion procedure in the detection steps of the present invention is counterstaining of the microscope slide with fluorescent dyes (for fluorescent tags) or chromophoric dyes (for radio-autoradiographic detection or enzymatic generation of insoluble chromophores) which emit or absorb with different spectral characteristics than the analyte-specific signals and which highlight cell structures, especially in cells which lack target nucleic acid sequence. Especially preferred for examination of insoluble blue dye deposits by transmission microscopy is counterstaining by nuclear fast red, standard in the histochemical and cytochemical art. The methods for examining stained in situ PCR preparations by transmission or fluorescence microscopy are well known in the histochemical and cytochemical art, as are methods of recording permanently the microscopic image photographically or via digitized video images.

When the first, second, or third aspects of the invention have been applied to fixed cells suspended in a PCR tube, an alternative detection mode to attachment to a slide for microscopic examination is direct flow cytometry of the suspended cells. Flow cytometry is best adapted to fluorescent signals, whether incorporated into amplified nucleic acid during in situ PCR or attached to amplified nucleic acid by probe hybridization post-PCR. In either case, it is important that the cells be washed by sedimentation and resuspension in tag-free buffered aqueous solvent to assure that tag not associated with amplified nucleic acid is completely removed. Flow cytometric methods, well known to cell biologists, are useful primarily for counting the proportions of cells containing and lacking tag, although they also can record the quantitative distribution of tag among cells.

The preferred mode of effecting the sample block and instrument aspects of the invention is to modify the manufacturing procedure for conventional thermal cycler sample blocks to change just the top surface so that it is optimized for heat flow to and from microscope slides. Two very distinct designs are provided. One, for in situ PCR applications where very few slides are to be run simultaneously, the top surface is designed to create flat horizontal areas large enough to hold slides so that the large dimensions (height and width) are horizontal. These flat areas may be recessed in shallow wells which hold a mineral oil vapor barrier covering the slides. The areas must be at least about 16 mm wide and 77 mm long to fit conventional glass microscope slides. The wells must be at least about 2 mm deep to fit a slide plus coverslip plus vapor banker. This design is compatible with either the first, second, or third aspect of the invention.

Two, for in situ PCR applications where many slides are to be run simultaneously, the block is designed to contain many narrow, deep, vertical or approximately vertical slots, sized to hold slides inserted edgewise with minimal space separating the slide from metal surfaces facing its top and bottom surfaces. The intervening space normally will be filled with mineral oil or another nonvolatile liquid to provide a vapor barrier and efficient heat transfer during thermal cycling. The plane of a slot may be inclined from the vertical by as much as about 45° in order to use the force of gravity to assure that one surface of the slide touches the metal of the sample block. Slots must be about 15 mm deep, at least 77 mm long, and at least 2 mm wide to fit a conventional slide plus a cover slip. This design is compatible with the second and the third aspects of the invention but is not preferred with the first because it blocks rapid access to the in situ PCR preparation for cover slip removal, manual addition of the missing PCR reagent(s), and cover slip replacement.

Many different thermal cyclers are commercially available, each with distinct sample block design. However, these sample block designs can be described in terms of several general features: (a) composition: practically all are made of metal, preferably aluminum, to promote durability and rapid heat transfer; (b) shape and overall dimensions of length, width, and thickness; (c) bottom and occasionally side surfaces designed to integrate with the heating and cooling mechanisms which determine block temperature when the thermal cycler is operating; (d) a top surface containing many wells dimensioned to hold tightly the small plastic microcentrifuge tubes, preferably of about 0.5 ml capacity but occasionally holding about 1.5 ml, which are commonly used to hold nucleic acid amplification reactions; (e) occasionally one or a few small wells in one surface designed to hold tightly a thermocouple or thermistor probe which feeds back the sample block temperature to the thermal cycler control circuitry.

A preferred mode of realizing the third aspect of the invention is to change only the top surface of the sample block, leaving the other design features (except possibly block thickness) substantially unchanged in order to minimize the impact of the invention on thermal cycler manufacture and performance. Also preferred is to render the sample block of the invention equal in mass to the conventional sample block of the thermal cycler in question, to minimize impact on heating and cooling kinetics.

Thermal cycler sample blocks most commonly are manufactured by machining into a single metal block, for example with a rotary mill, exact dimensions, wells, and other contours needed to integrate with the rest of the thermal cycler. Holes for bolting the block to the rest of the thermal cycler may be made with a drill press. The same manufacturing procedures are suitable for the sample block of the present invention. However, the rectilinear shape of wells adapted to fit microscope slides tightly is also easily produced by stamping or machining (including laser and water jet cutting) of relatively thin sheets of metal which are bolted together to create a laminated assembly. The entire block may be laminated; or just the top portion, holding the microscope slide wells, can be laminated and bolted to a solid bottom portion which contains the features of the block which integrate with the rest of the thermal cycler.

Also preferred for the third aspect of the invention is a thermal cycler sample block design which includes both wells optimized for microscope slides and wells designed to hold conventional nucleic acid amplification reaction tubes. Preferably the reaction tube wells will occupy one or several rows along the edges of the sample block, reserving the central area of the sample block for microscope slide wells. This mode also is best realized by leaving the other sample block features, including mass of metal, unchanged. Manufacture is most simply performed by machining, because of the cylindrical symmetry of reaction tube wells.

A few commercially available thermal cyclers and published thermal cycler designs avoid metal sample blocks and immerse conventional PCR tubes in a rapidly moving stream of hot or cold air, water, or other heat-transfer fluid. Such designs are easily adapted to microscope slides by replacing the tube holders with a metal wire or plastic lattice which holds slides firmly in the stream of heat-transfer fluid. Preferably, the slides are oriented so that their smallest dimension (thickness) faces the fluid flow and the dominant fluid flow vector lies in a plane which parallels the plane of their larger dimensions (width and length). Slight canting of the microscope slides to the dominant fluid flow vector can create mild turbulence which helps to ensure uniform heat transfer.

In the event that the thermal cycler contacts microscope slides directly with a moving heat transfer fluid, it is necessary to isolate the slides from the heat-transfer fluid by a thin barrier which blocks material transfer between the in situ PCR preparation and the heat-transfer fluid. Otherwise the preparation may be desiccated or experience wash-out of PCR reagents. Preferred barriers are envelopes of a thin, water-impermeant plastic with high thermal conductivity, such as a fluorocarbon, a polyurethane, a polyolefin, a polyimide, or a polyamide. The envelopes must be sealed in a way which prevents leakage of fluid or water vapor into or out of them. Either a water-resistant adhesive or a tight clip may serve adequately to seal the envelope. If the heat-transfer fluid is a liquid, one edge of the envelope may project above the liquid into the vapor space over it. As an alternative to an envelope, the vapor barrier may comprise a thin sheet of plastic with approximately the length and width of a microscope slide, carrying hot-water-resistant adhesive applied in a narrow strip around all edges on one face. The sheet is pressed tightly to the top face of the microscope slide before thermal cycling is started, and can be peeled off afterward for detection processing. It may even replace the coverslip.

From the above description and the following examples, one of ordinary skill in the art can appreciate the many diverse aspects of the present invention as encompassed by the following claims.

EXAMPLE 1

In Situ PCR and Hybridization Detection of HPV Integrated into Human Genomic DNA Cells of the stable human cervical cancer cell line, SiHa (ATCC HTB 35), containing one integrated copy of human papilloma virus (HPV) type 16 genome per human genome, were grown to density of about $10^5$ cells/mL in Eagle's minimal essential medium with non-essential amino acids, sodium pyruvate, and 15% fetal bovine serum, washed two times in Tris-buffered saline, adjusted to an approximate density of $10^4$ cells/mL, and stirred overnight at room temperature in 10% (vol/vol) formaldehyde in phosphate buffer. The formaldehyde-fixed cells were centrifuged at 2,000 rpm for 3 minutes, and the pellet was embedded in paraffin. Microtome sections (4 µm thickness) of the paraffin block were attached to glass microscope slides which had been dipped in 2% 3-aminopropyltriethoxysilane (Aldrich Chemical Co.) in acetone by floating the sections in a water bath. After attachment, sections were deparaffinized and proteolytically digested with reagents from the Viratype® in situ Tissue Hybridization Kit (Life Technologies, Inc., Gaithersburg, Md.) following the manufacturer's instructions. (The equivalent reagents and methods of the Oncor S6800-kit, Oncor, Inc., Gaithersburg, Md., could have been used instead). Slides were placed in hand-made aluminum foil boats, approximate dimensions of 8×3×1 mm; and each set of four sections (per slide) was overlaid with 5 to 10 µl of PCR solution (see below). A plastic coverslip then was placed over each four section in situ PCR preparation. For conventional in situ PCR, the coverslip was anchored to the slide with a drop of nail polish, the slide was covered with approximately 1 ml of mineral oil, the foil boat was laid on top of the aluminum sample block of a PCR thermal cycler (Perkin Elmer Cetus Instruments, Norwalk, Conn.), and thermal cycling was started. For manual Hot Start™ in situ PCR, the boat containing a slide (with coverslip) was heated to 82° C. and held at that thermal cycler temperature while the coverslip was lifted, 2 µl of the missing PCR reagents (see below) were distributed over the surface of the preparation, the coverslip was replaced and attached to the slide with a drop of nail polish, and approximately 1 ml of mineral oil pre-heated to 82° C. was laid over the slide and coverslip in the boat. Then the normal thermal program was resumed.

The pH 8.3 PCR solution contained 10 mM TrisCl, 50 mM KCl, 4.5 mM $MgCl_2$, 20 mM of each dNTP, 0.2 unit/µL of AmpliTaq® DNA polymerase (Perkin Elmer Cetus Instruments, Norwalk, Conn.), and 6 µM of each primer. For "single primer pair" experiments, the primers were PV 1 and PV2, dictating a 449 bp product from the HPV type 16 genome. For "multiple primer pair" experiments, primers PV 1 to PV7, dictating a series of overlapping approximately 450 bp PCR products covering a total sequence length of 1247 bp, were used. All primer sequences are given in the Table below.

| Primer | SEQ ID No. | Position of First Nucleotide | Sequence |
| --- | --- | --- | --- |
| PV1 (5') | 1 | 110 | 5'-CAGGACCCACAGGAGCGACC |
| PV2 (3') | 2 | 559 | 5'-TTACAGCTGGGTTTCTCTAC |
| PV3 (5') | 3 | 501 | 5'-CCGGTCGATGTATGTCTTGT |
| PV4 (3') | 4 | 956 | 5'-ATCCCCTGTTTTTTTTTCCA |
| PV5 (5') | 5 | 898 | 5'-GGTACGGGATGTAATGGATG |
| PV6 (3') | 6 | 1357 | 5'-CCACTTCCACCACTATACTG |
| PV7 (5') | 7 | 1300 | 5'-AGGTAGAAGGGCGCCATGAG |

For conventional in situ PCR, all of the components listed above were present in the PCR solution initially added to the histochemical sections. For manual Hot Start™ in situ PCR, the solution initially added to the sections lacked primers and Taq polymerase. These reagents were added separately in 2 µl of 10 mM TrisCl, 50 mM KCl, pH 8.3 after the slide had been heated to 82° C. For the first thermal cycle, denaturation was performed for 3 minutes at 94° C., and annealing/extension was performed for 2 minutes at 55° C.; the remaining 39 cycles consisted of 1 minute denaturation at 94° C. and 2 minutes annealing-extension.

After DNA amplification, mineral oil was removed by dipping in xylene, the cover slip was removed, and the mounted sections were dried in 100% ethanol. Each slide was incubated with 10 µl of a 500 ng/ml solution of biotinylated HPV type 16specific polynucleotide probe (Viratype Kit, Life Technologies, Inc.) in 0.03 M Na citrate, 0.30 M NaCl, pH 7.0, 5% dextran sulfate, 50% formamide at 100° C for 5 minutes and then 37° C. for at 2 hours; then the slide was treated with an alkaline phosphatase-streptavidin conjugate and the phosphatase substrates, 5-bromo-4-chloro- 3-indolyl phosphate (BCIP) and nitro blue tetrazolium (NBT), according to the instructions of the supplier of the S6800 Staining Kit (Oncor, Gaithersburg, Md.). After enzymatic detection of biotinylated probe captured on the sections, the sections were counterstained with nuclear fast red for 5 minutes. The following results were obtained in this experimental system, when the stained slides were examined by transmission microscopy under 40–400 X magnification. In conventional in situ PCR, single-copy HPV targets in SiHa cells were not detectable with a single primer pair but showed up clearly in most nuclei with multiple primer pairs. In manual Hot Start™ in situ PCR, a single primer pair stained about 80% of the cell nuclei more strongly than did multiple primer pairs in the conventional method. The other 20% may have been damaged during sectioning. The previously published conclusion that in situ PCR requires multiple primer pairs specifying overlapping targets is thus invalid. The practical, and in fact improved, performance of a single primer pair greatly increases the utility of in situ PCR.

EXAMPLE 2

In Situ PCR Hybridization Detection of HIV-I Integrated into Human Genomic DNA The human T lymphocytic cell line, H9 (ATCC CRL 8543), was grown to a density of about $10^6$ cells/ml in complete RPMI medium, infected with HIV-1 as described in Basic Virological Techniques, pp. 66–69, and incubated for four days at room temperature. Approximately $10^4$ cells from this incubation were formaldehyde-fixed, paraffin-embedded, sectioned (4 µm thickness), mounted on glass slides, and proteolyticaily permeabilized as in Example 1. Conventional and manual Hot Start™ in situ PCR were performed as in Example 1 except that a single primer pair, SK38 and SK39 (Perkin Elmer Cetus Instruments, Norwalk, Conn.) specifying a 115 bp target from the HIV-1 gag region, was used. PostoPCR processing was as in Example 1, except that the probe, SK19 (Perkin Elmer Cetus Instruments), was labeled with digoxigenin- 11-dUTP using random primers, using the reagents and following the instructions of Boehringer Mannheim (Indianapolis, Ind.), manufacturer of the tagged dNTP and the Genius™ labeling kit. Staining of the probed microscope slide was with an alkaline phosphatase-anti-digoxigenin conjugate and BCIP/NBT chromogens, also as directed by Boehringer Mannheim.

Microscopic examination of the slide showed that about 90% of cell nuclei were BCIP/NBT stained after manual Hot Start™ in situ PCR; conventional in Situ PCR yielded no stained nuclei. Even a 115 bp product appears to be detectable nonisotopically by (and only by) the manual Hot Start™ methodological improvement.

EXAMPLE 3

In Situ PCR Specificity Improvement Resulting from the Hot Start Method

Microscope slides carrying histochemical sections of embedded fixed SiHa cells were prepared as in Example 1. The sections were augmented with approximately 50 µl of human peripheral leukocytes (approximately 5,000 cells/ml) from an HPV-negative donor, prepared from buffy coat and deposited on the slide by cytospin. The added cells were fixed for 5 minutes at room temperature in 10% formaldehyde in phosphate buffer. The slides were subjected to conventional or manual Hot Start™ in situ PCR as described in Example 1, except that the dNTPs were augmented with 5 mM digoxigenin- 11-dUTP (Boehringer Mannheim). HPV primer pairs PV1 and PV2 were used.

After DNA amplification, all digoxigenin-tagged DNA which was not removed during washing and dehydration was stained with an alkaline phosphatase-antidigoxigenin conjugate and phosphatase substrates, BCIP and NBT, as recommended by Boehringer Mannheim, supplier of the staining reagents, except that reagent volumes were scaled down approximately 95% to accommodate histochemical sections rather than Southern blotting membranes. After staining of the amplified DNA, the leukocytes were immunohistochemically stained by a pair of mouse monoclonal primary antibodies against leucocyte common antigen (DAKO-LCA, containing antibodies pD7/26 and 2BN; DAKO-PATTS) and a Histostain-SP kit for detecting mouse primary antibody (Zymed Laboratories Inc., South San Francisco, Calif.). This kit uses a biotinylated anti-mouse secondary antibody, horseradish peroxidase-streptavidin, and the chromogenic peroxidase substrate, aminoethylcarbazole. Both the primary antibodies and the staining kit were used according to the manufacturer's instructions.

Microscopic examination showed that manual Hot Start™ in situ PCR stained about 80% of SiHa cell nuclei and no leucocyte nuclei, demonstrating the specificity and sensitivity of the Hot Start™ procedure, even with a single primer pair. In contrast, conventional in situ PCR was so nonspecific that all cells, both SiHa and leucocyte, were stained, indicated that considerable non-target-directed amplification occurs when the Hot Start™ procedure is not used. Although target-specific probes can distinguish specific and nonspecific amplified DNA after in situ hybridization (see Example 1), the present Example demonstrates that the Hot Start™ method can render probing unnecessary, greatly simplifying detection and thereby enhancing the practicality of in situ PCR even more.

We claim:

1. A method for in situ PCR amplification of target nucleic acid wherein said amplified nucleic acid is spatially confined to individual cells originally containing said target nucleic acid, said method comprising:

(a) fixing cells thought to contain said target nucleic acid in a fixative selected from the group consisting of formalin, formaldehyde, paraformaldehyde and glutaraldehyde;

(b) contacting said fixed cells with a proteinase;

(c) adding a first subset of PCR reagents to said fixed cells, said first subset of PCR reagents comprising a portion of the PCR reagents necessary to allow PCR to proceed;

(d) incubating in a moist environment said fixed cells and said first subset of PCR reagents at a temperature between 50° C. and about 80° C.;

(e) adding a second subset of PCR reagents to said fixed cells, said second subset of PCR reagents comprising the PCR reagents which are missing from said first subset of PCR reagents and which are necessary to allow PCR to proceed; and (f) subjecting said fixed cells and said first and said second subsets of PCR reagents in a moist environment to thermal cycling sufficient to amplify said target nucleic acid.

2. A method in accordance with claim 1 wherein said cells are animal cells.

3. A method in accordance with claim 1 wherein said fixative is formalin.

4. A method in accordance with claim 3 wherein said formalin is buffered formalin.

5. A method in accordance with claim 4 wherein said buffered formalin is 10% formalin in 0.1 M sodium phosphate buffer, pH 7.0.

6. A method in accordance with claim 1 wherein said fixed cells re, side within a histochemical section or cytochemical smear attached to a microscope slide.

7. A method in accordance with claim 1 wherein prior to step (d) said fixed cells are covered with a cover slip.

8. A method in accordance with claim 1 wherein said fixed cells are attached to a microscope slide prior to step (c).

9. A method in accordance with claim 1 wherein said first subset of PCR reagents consists of all PCR reagents except a nucleic acid polymerase.

10. A method in accordance with claim 1 further comprising:

(g) detecting said amplified nucleic acid in a manner which locates it in the individual cells originally containing said target nucleic acid sequence.

11. A method in accordance with claim 10 wherein said fixed cells are attached to a microscope slide between steps (f) and (g).

12. A method for in situ PCR amplification of target nucleic acid wherein said amplified nucleic acid is spatially confined to individual cells originally containing said target nucleic acid, said method comprising:

(a) fixing cells thought to contain said target nucleic acid in a fixative selected from the group consisting of formalin, formaldehyde, paraformaldehyde and glutaraldehyde;

(b) contacting said fixed cells with a proteinase;

(c) adding a complete set of PCR reagents and a single-stranded DNA binding protein to said fixed cells; and (d) subjecting said fixed cells in a moist environment to thermal cycling sufficient to amplify said target nucleic acid.

13. A method in accordance with claim 12 wherein said cells are animal cells.

14. A method in accordance with claim 12 wherein said fixative is formalin.

15. A method in accordance with claim 14 wherein said formalin is buffered formalin.

16. A method in accordance with claim 15 wherein said buffered formalin is 10% formalin in 0.1 M sodium phosphate buffer, pH 7.0.

17. A method in accordance with claim 11 wherein said singles stranded DNA binding protein is bacteriophage T4 gene 32 protein.

18. A method in accordance with claim 12 wherein said single-stranded DNA binding protein is the 19 kilodalton SSB from *E. coli*.

19. A method in accordance with claim 12 wherein said fixed cells reside within a histochemical section or cytochemical smear attached to a microscope slide.

20. A method in accordance with claim 12 wherein prior to step (c) said fixed cells are covered with a cover slip.

21. A method in accordance with claim 12 wherein prior to step (c) said fixed cells are covered with a vapor barrier.

22. A method in accordance with claim 12 further comprising:

(e) detecting said amplified nucleic acid in a manner which locates it in the individual cells originally containing said target nucleic acid sequence.

23. A method in accordance with claim 22 wherein said fixed cells are attached to a microscope slide prior to step (c).

24. A method in accordance with claim 22 wherein said fixed cells are attached to a microscope slide between steps (d) and (e).

* * * * *

UNITED STATES PATENT AND TRADEMARK OFFICE
CERTIFICATE OF CORRECTION

PATENT NO. : 5,538,871
DATED : July 23, 1996
INVENTOR(S) : Gerard J. Nuovo and Will Bloch It is certified that error appears in the above-indentified patent and that said Letters Patent is hereby corrected as shown below:

In column 8, line 43, please delete "Silo" and insert therefor --situ--.

In column 9, line 24, please delete "nounally" and insert therefor --normally--.

In column 20, line 19, please delete "PostoPCR" and insert therefor --Post-PCR--.

In column 23, Claim 1, line 40 please delete "in situ" and insert therefor --*in situ*--.

In column 24, Claim 6, line 47 please delete "re,side" and insert therefor --reside--.

In column 25, Claim 17, line 20 please delete "11" and insert therefor --12--.
Column 25,
Claim 17, line 21 please delete "singles stranded" and insert therefor --single stranded--.

Signed and Sealed this

Fourth Day of February, 1997

*Attest:*

BRUCE LEHMAN

*Attesting Officer*     *Commissioner of Patents and Trademarks*